(12) United States Patent
Butchko et al.

(10) Patent No.: US 7,538,232 B2
(45) Date of Patent: May 26, 2009

(54) PROCESS FOR THE ASYMMETRIC SYNTHESIS OF DULOXETINE

(75) Inventors: Mark Anthony Butchko, Frankfort, IN (US); Alain Merschaert, Mont Saint Guibert (BE); Kenneth Philip Moder, West Lafayette, IN (US)

(73) Assignee: Eli Lilly and Company, Indianapolis, IN (US)

( * ) Notice: Subject to any disclaimer, the term of this patent is extended or adjusted under 35 U.S.C. 154(b) by 375 days.

(21) Appl. No.: 11/275,613

(22) Filed: Jan. 19, 2006

(65) Prior Publication Data

US 2007/0167636 A1    Jul. 19, 2007

(51) Int. Cl.
*C07D 333/12*    (2006.01)
(52) U.S. Cl. ........................................................ 549/75
(58) Field of Classification Search .................... 549/75
See application file for complete search history.

(56) References Cited

U.S. PATENT DOCUMENTS 5,023,269 A    6/1991    Robertson et al.
5,362,886 A    11/1994   Berglund

FOREIGN PATENT DOCUMENTS

| WO | WO-00/61540 | 10/2000 |
| WO | WO-2004/056795 A1 | 7/2004 |
| WO | WO 2004056795 A1 * | 7/2004 |
| WO | WO 2006/071868 A2 | 7/2006 |

OTHER PUBLICATIONS

Disclosure: "A new synthetic process for manufacture of duloxetine", Poster, Apr. 11, 2005.

* cited by examiner

*Primary Examiner*—Rei-Tsang Shiao
*Assistant Examiner*—Joseph R Kosack
(74) *Attorney, Agent, or Firm*—Tonya L. Combs

(57) ABSTRACT

This invention provides an improved asymmetric process for the synthesis of duloxetine involving arylation of Compounds of Formula I.

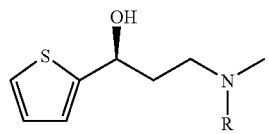

9 Claims, No Drawings

PROCESS FOR THE ASYMMETRIC SYNTHESIS OF DULOXETINE

BACKGROUND OF THE INVENTION

This invention relates to the fields of pharmaceutical chemistry and synthetic organic chemistry. Specifically, the invention is an improved process for the synthesis of duloxetine, (S)-(+)N-methyl-3(1-naphthalenyloxy)-3-(2-thienyl) propanamine. Compounds of Formula I:

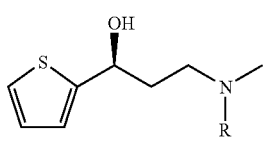

wherein R is methyl or hydrogen are intermediates useful in the synthesis of duloxetine. Duloxetine hydrochloride is a pharmaceutical currently marketed in the United States as an anti-depressant and inhibits the uptake of both norepinephrine and serotonin. Duloxetine is disclosed in U.S. Pat. Nos. 5,023,269 and 4,956,388 by Robertson, et al. The synthesis of duloxetine is discussed in more detail by Berglund, R. A., Org. Proc. Res. Devel., 1, 328 (1997) and Deeter, et al., in Tetrahedron Letters, 31(40), 7101-04 (1990) and aspects patented in U.S. Pat. Nos. 5,362,866 and 5,491,243.

Additional synthetic schemes and processes are reported for conversion to duloxetine. Several of these syntheses proceed via a monomethylaminoalcohol (Compound Ia in Scheme 1 below). As shown in Scheme 1, Compound Ia is arylated with 1-fluoronaphthalene to give Compound A, which, is duloxetine.

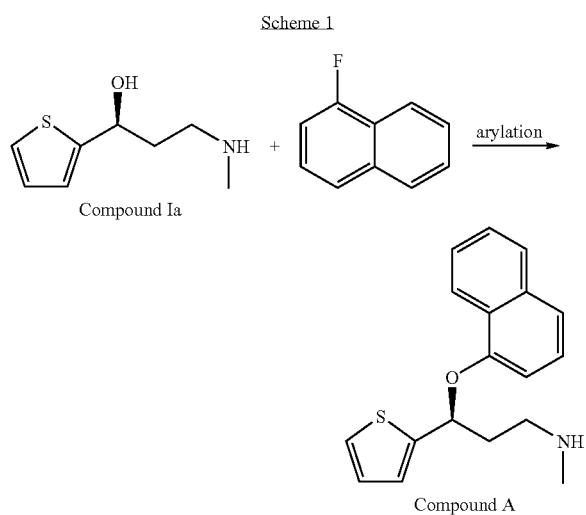

U.S. Pat. No. 5,362,866 discloses a process to synthesize duloxetine via arylation of a dimethylamino alcohol, Compound Ib. In Scheme 2 below, Compound Ib is arylated with 1-fluoronaphthalene to give Compound B, which may be recovered as the phosphoric acid salt if desired. The dealkylation of Compound B yields duloxetine as a final product.

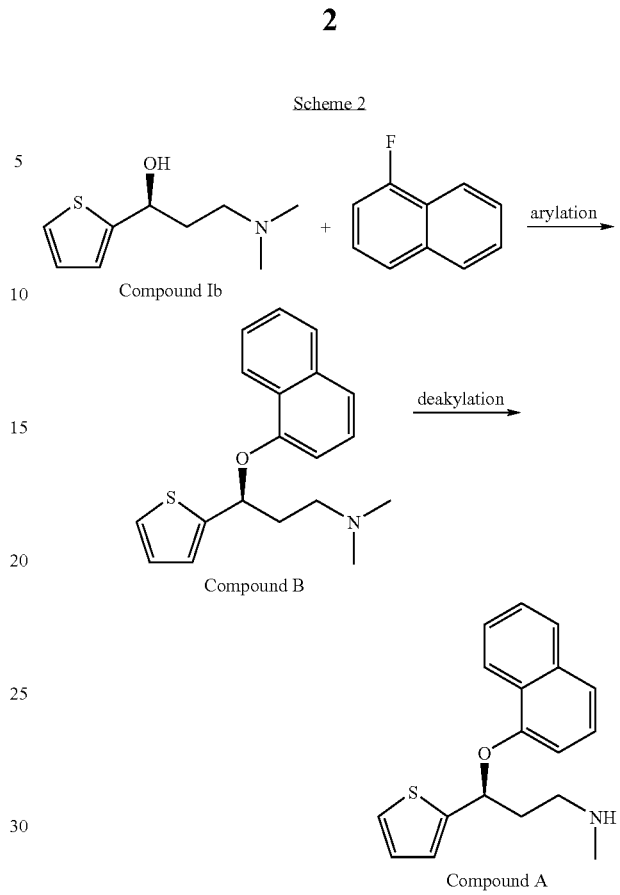

To date most processes utilized to synthesize duloxetine proceed via an arylation step involving sodium hydride. Sodium hydride is a strong base that can pose environmental and safety hazards which are exacerbated upon manufacturing scale-up. Known processes to synthesize duloxetine also utilize DMSO. DMSO can form dimsyl anion when coupled with sodium hydride. It is reported that dimsyl anion can cause racemization, which poses difficulty as only one enantiomer, (S)-duloxetine hydrochloride, is the desired product. Moreover, thermochemical hazards are associated with the degradation of dimsyl anion. Therefore, an improved process that avoids the use of sodium hydride and generation of dimsyl anion is needed.

Use of DMSO alone as a solvent in the present invention results in complete racemization. Further, use of DMSO in a large scale manufacturing process is associated with increased cost of recovery, or of incineration. DMSO is also associated with $SO_x$ emissions, posing an additional environmental concern. An improved process that utilizes less DMSO is needed.

International Patent Application Publication WO 2004/056795, published Jul. 8, 2004, discloses a process for the synthesis of duloxetine utilizing a weaker base than sodium hydride but still utilizing DMSO. However, the process described in WO 2004/056795 describes the use of a phase transfer catalyst to prevent racemization. The toxicity of phase transfer catalysts such as 18-crown-6 has been reported. See Takayama, K. et al, Chem. Pharm. Bull. 25(11), 3125 (1977), and Hendrixson, R. et. al, Toxicol. Appl. Pharmacol., 44, 263 (1978). International Patent Application Publication WO 00/61540, published Oct. 19, 2000, describes arylation of 3-hydroxy-3-arylpropylamines. However, the process described therein requires the use of either 1,3-dimethyl-2-imidazolidinone or N-methylpyrrolidinone.

Significant or complete racemization is observed at known conditions when using potassium hydroxide for the arylation of Compounds of Formula I in DMSO with 1-fluoronaphthalene. Surprisingly, almost no racemization is observed when Compounds of Formula I are arylated via the process of the instant invention. Further, a surprising correlation was discovered between suitable solvent system parameters and amount of racemization observed. The process of the present invention effects arylation of Compounds of Formula I with 1-fluoronaphthalene utilizing potassium hydroxide and particular organic solvents, such as glymes or mixtures of DMSO and toluene. The present invention provides improved reaction conditions for this arylation whereby chiral integrity, purity, and yield are preserved, dimsyl anion is not formed, a phase transfer catalyst is not required, and numerous safety and environmental improvements observed by removal of the requirement of sodium hydride and utilizing less DMSO.

BRIEF SUMMARY OF THE INVENTION

This invention includes a process for preparing (S)-(+)-N-methyl-3-(1-naphthalenyloxy)-3-(2-thienyl)propanamine comprising reacting (S)-3-Methylamino-1-(2-thienyl)-1-propanol with potassium hydroxide and 1-fluoronaphthalene in an organic solvent or mixture of organic solvents.

Another embodiment of this invention includes A process for preparing (S)-(+)-N-methyl-3-(1-naphthalenyloxy)-3-(2-thienyl)propanamine comprising reacting (S)-3-Methylamino-1-(2-thienyl)-1-propanol with potassium hydroxide and 1-fluoronaphthalene in an organic solvent or mixture of organic solvents wherein the product has a % R preferably less than 20%, more preferably less than 10%, and most preferably less than 6%.

A further embodiment of the present invention includes a process for preparing (S)-(+)-N-methyl-3-(1-naphthalenyloxy)-3-(2-thienyl)propanamine comprising reacting (S)-3-Methylamino-1-(2-thienyl)-1-propanol with potassium hydroxide and 1-fluoronaphthalene in an organic solvent or mixture of organic solvents wherein the organic solvent is a mixture of DMSO and toluene.

Additionally, the present invention provides a process for preparing (S)-(+)-N-methyl-3-(1-naphthalenyloxy)-3-(2-thienyl)propanamine comprising reacting (S)-3-Methylamino-1-(2-thienyl)-1-propanol with potassium hydroxide and 1-fluoronaphthalene in an organic solvent or mixture of organic solvents further comprising heating the mixture to a temperature of from about 40° C. to 110° C. for about 1 hour to 48 hours.

This invention also includes a process for preparing (S)-(+)-N,N-dimethyl-3-(1-naphthalenyloxy)-3-(2-thienyl)propanamine comprising reacting (S)-(−)-N,N-dimethyl-3-(2-thienyl)-3-hydroxypropanamine with potassium hydroxide and 1-fluoronaphthalene in an organic solvent or mixture of organic solvents.

A further embodiment of this invention is a process for preparing (S)-(+)-N,N-dimethyl-3-(1-naphthalenyloxy)-3-(2-thienyl)propanamine comprising reacting (S)-(−)-N,N-dimethyl-3-(2-thienyl)-3-hydroxypropanamine with potassium hydroxide and 1-fluoronaphthalene in an organic solvent or mixture of organic solvents wherein the product has a % ΔR preferably less than 20%, more preferably less than 10%, and most preferably less than 6%.

This invention also includes a process for preparing (S)-(+)-N,N-dimethyl-3-(1-naphthalenyloxy)-3-(2-thienyl)propanamine comprising reacting (S)-(−)-N,N-dimethyl-3-(2-thienyl)-3-hydroxypropanamine with potassium hydroxide and 1-fluoronaphthalene in an organic solvent or mixture of organic solvents wherein the organic solvent is glyme, diglyme, triglyme, or tetraglyme.

Moreover, this invention includes a process for preparing (S)-(+)-N,N-dimethyl-3-(1-naphthalenyloxy)-3-(2-thienyl) propanamine comprising reacting (S)-(−)-N,N-dimethyl-3-(2-thienyl)-3-hydroxypropanamine with potassium hydroxide and 1-fluoronaphthalene in an organic solvent or mixture of organic solvents further comprising heating the mixture to a temperature of from about 80° C. to 120° C. for about 1 hour to 24 hours.

Also contemplated within the scope of the present invention is a process for preparing (S)-(+)N-methyl-3(1-napthalenyloxy)-3-(2-thienyl)propanamine comprising reacting a Compound of Formula I with 1-fluoronaphthalene and potassium hydroxide, in glymes or a in a mixture of toluene and DMSO.

DETAILED DESCRIPTION OF THE INVENTION

As used herein, the term "ee" or "enantiomeric excess" refers to the percent by which one enantiomer, $E_1$ is in excess in a mixture of both enantiomers ($E_1+E_2$), as calculated by the equation $\{(E_1-E_2)\div(E_1+E_2)\}\times100\%=ee$. The term "% R" refers to the amount of (R)-enantiomer formed. The term "% ΔR" refers to the difference in the amount of (R)-enantiomer in the product and the amount of (R)-enantiomer in starting material. For example if Compound Ia % R=0.2%, and upon arylation, Compound A product % R=2.3%, then % ΔR=2.1%. The term "glymes" refers to glyme, diglyme, triglyme, or tetraglyme. The term "suitable solvent system" refers to glymes or a mixture of DMSO and toluene.

The arylation is prepared by adding a Compound of Formula I, potassium hydroxide, and 1-fluoronaphthalene, to a suitable solvent system, and preferably applying heat. The order and manner of combining the reactants may be varied. Temperatures may range from room temperature to a temperature near the boiling point of the suitable solvent system. The mixture is then quenched and separated using procedures well known to the skilled artisan. When utilizing Compounds of Formula Ib in the present invention, the product may be optionally recovered as the phosphoric acid salt.

The skilled artisan appreciates that conditions of the present invention may vary according to solvent system, agitation rate, the solid state of materials used, including the use of potassium hydroxide in powdered form, flakes, or pellets. These variations are contemplated and encompassed within the present invention. A preferred embodiment of the invention involves dissolving Compound Ib in glymes, preferably diglyme. When Compound Ib has been dissolved, preferably at ambient temperature such as from about 10° to about 35° C., a portion of potassium hydroxide is added. The amount of potassium hydroxide is preferably 3-6 equivalents, most preferably 4-5 equivalents. The reaction mixture is then optionally stirred for a period, such as from about 0 to about 60 minutes, and then combined with 1-fluoronaphthalene. An additional period of stirring is provided after the addition of the 1-fluoronaphthalene. A small amount of excess 1-fluoronaphthalene, such as from about 1% to about 25% excess, may advantageously be used to assure consumption of the Compound Ib starting material.

When the 1-fluoronaphthalene has been added, the reaction mixture is preferably warmed, to a temperature from 40° to 150° C., preferably from about 85° to about 120° C., and most preferably from about 115° to about 120° C., and the mixture is stirred for a period of time, such as from about 1 to about 24 hours, most preferably from about 3 to about 6 hours. The desired product is then isolated by conventional extractions and filtrations, and, if it is desired to do so, the product may advantageously be converted to the phosphoric acid salt by reaction with phosphoric acid in an organic solvent such as ethyl acetate.

Another preferred embodiment involves a substantially analogous process to that described immediately above, in which Compound Ia is utilized as the starting material, and the suitable solvent system is a mixture of toluene and DMSO, with mixtures greater than 3:1 ratio of toluene to DMSO by volume being preferred, and mixtures greater than 9:1 most preferred, and a mixture of 10:1 most especially preferred. When Compound Ia has been dissolved, preferably at ambient temperature, a portion of potassium hydroxide is added. The amount of potassium hydroxide is preferably 3-6 equivalents, most preferably 4-5 equivalents. The reaction mixture is then optionally stirred for a period, such as from about 0 to about 60 minutes, and then combined with 1-fluoronaphthalene. A small amount of excess 1-fluoronaphthalene, such as from about 1% to about 40% excess, may advantageously be used to assure consumption of the Compound Ia starting material. When the 1-fluoronaphthalene has been added, the reaction mixture is preferably warmed to a temperature from 40° to 110° C., most preferably from 75° C. to about 95° C., and then stirred for a period of time, such as from 1 to about 48 hours, most preferably from 6 to about 12 hours. The desired product is then isolated by conventional extractions and filtrations, and, if it is desired to do so, the product may be converted to the hydrochloride salt in an organic solvent such as ethyl acetate.

The advantage of the present invention is found in its ability to prepare the desired product with relatively low racemization, and without the use of dimsyl anion-forming reagents or potentially toxic phase transfer catalysts.

Compounds of Formula I are available by the teachings of the prior art. See Preparation 1, U.S. Pat. No. 5,362,886, and International Patent Application Publication WO03/062219. Upon the arylation of Compound Ib, the product may then be demethylated and treated with hydrochloric acid to obtain duloxetine hydrochloride. See Preparation 2, U.S. Pat. No. 5,362,886. Compound Ia may be converted to duloxetine as described in Liu, H. et. al., *Chirality*, 12, 26 (2000) and Wheeler, W. J.; Kuo, F. S. *Labelled Compd. Radiopharm.*, 36, 213 (1995).

Table 1 below demonstrates that arylation of Compounds of Formula 1 with 1-fluoronaphthalene in DMSO utilizing KOH produces high amounts of racemization. This data is generated for a Compound of Formula Ia using Procedure A.

Procedure A

Charge Radleys Carousel Reaction Station™ tubes with 0.342 g (2 mmol) of Compound Ia, 0.264 mL (2.4 mmol, 1.2 equiv) 1-fluoronaphthalene and 0.48 g (8 mmol, 4 equiv, corrected for ca. 90% potency) powdered KOH. The solvent composition is adjusted by a) adding toluene (3 mL) in several tubes followed by variable amounts of DMSO, ranging from 0.2 mL (toluene/DMSO=15:1 v/v) to 1 mL (toluene/DMSO=3:1 v/v) and b) in one tube, adding DMSO alone (3 mL).

Fit the tubes in the Carousel Reaction Station™ under nitrogen and heat to 60° C. (internal T°) with magnetic stirring for 8 h. Monitor Compound Ia conversion by TLC and the % R enantiomer by chiral HPLC under the following conditions: column: Daicel, Chiralcel® OD-H, 5 microns, 4.6×250 mm internal diameter, 40° C.; solvent: 83% hexane+ 0.1% diethylamine (DEA)–17% isopropanol+0.1% DEA, 1 mL/min; detection UV 220 nm.

TABLE 1

| Starting Material | Base | Solvent | % R |
|---|---|---|---|
| Compound Ia | KOH | DMSO | 50% |
| Compound Ib | KOH | DMSO | 33% |

However, as demonstrated below in Table 2, when using a suitable solvent system of the present invention, levels of racemization drop precipitously without the use of a phase transfer catalyst.

TABLE 2

| Starting Material | Base | Solvent (ratio) | % ΔR |
|---|---|---|---|
| Compound Ia | KOH | Toluene/DMSO (3:1) | 16.3 |
| Compound Ia | KOH | Toluene/DMSO (6:1) | 2.1 |
| Compound Ia | KOH | Toluene/DMSO (15:1) | −0.2 |
| Compound Ib | KOH | Glyme | 0.2 |
| Compound Ib | KOH | Diglyme | 0.1 |
| Compound Ib | KOH | Triglyme | 0.4 |
| Compound Ib | KOH | Tetraglyme | 0.6 |

The data for compound Ia in Table 2 may be generated using Procedure A above. The data for Compound Ib in Table 2 involving glymes may be generated using a procedure substantially analogous to that set forth in Example 2.

Illustrative procedures of these processes is available in Examples 1 and 2 below and are not intended to limit the invention in any way. Herein and below, the terms used have their normal meanings unless otherwise designated. For example, "° C." refers to degrees Celsius; "DEA" refers to diethylamine; "h" or "hr" refers to hour or hours; "N" refers to normal or normality; "M" refers to molar or molarity; "mol" refers to mole or moles; "mmol" refers to millimole or millimoles; "g" refers to gram or grams; "mg" refers to milligram or milligrams; "mL" refers to milliliter or milliliters; "L" refers to liter or liters; etc.

EXAMPLE 1

Arylation of (S)-(−)-N,N-dimethyl-3(2-thienyl)-3-hydroxypropanamine

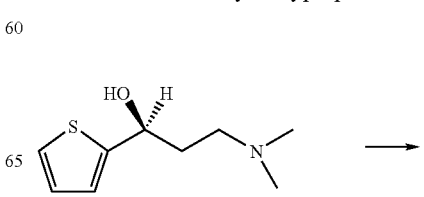

-continued

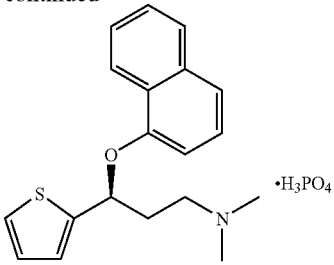

To a 25 mL 3-neck round bottom flask equipped with a condenser, $N_2$ inlet, thermocouple, and overhead stirrer charge Compound Ib (0.55 g, 3 mMol), powdered KOH (0.9 g, 14.2 mMol), diglyme (6 mL) and 1-fluoronaphthalene (0.5 mL). Heat the mixture with good agitation to 120° C. for 3 to 6 hrs. Cool to ambient temp. and dilute with water (6 mL) and EtOAc (6 mL). Separate layers, back extract aqueous with EtOAc (6 mL). Separate layers and combine organic layers. Place organic layers in a 25 mL 3-neck round bottom flask with overhead agitation. Slowly add 85% $H_3PO_4$ (0.25 mL). Seed after 10 drops have been added. Stir 5-15 minutes, complete acid addition and stir 1 hr. Filter and wash cake with EtOAc (10 mLs). Dry under reduced pressure to yield 1.0 g of the title compound. % ΔR:0.2. Monitor the % R enantiomer by chiral HPLC under the following conditions: Column; Diacel Chiralcel® OD-H, 5 micron silica, 4.6×250 mm internal diameter, 40° C.; Solvent: 95% hexane, 5% isopropanol+ 0.2% DEA, 1 mL/min; detection UV 280 nm.

EXAMPLE 2

Arylation of (S)-3-Methylamino-1-(2-thienyl)-1-propanol

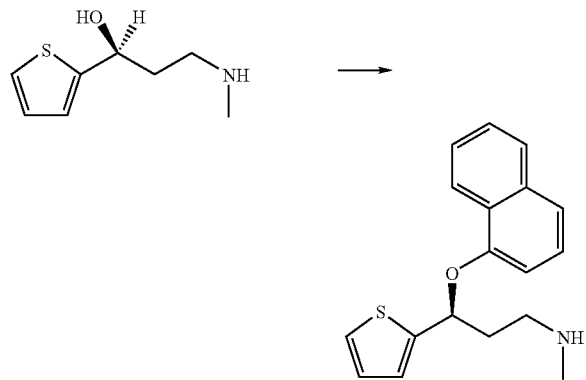

Combine Compound Ia (10.0 g, 58.5 mmol), potassium hydroxide (14.7 g, 235 mmol), and 1-fluoronaphthalene (10.8 g, 74.0 mmol) in toluene (100 ml) and DMSO (10 ml). Heat to about 85° C. with agitation. After 12 hours, cool the resulting mixture to ambient temperature and carefully add water (100 ml). Separate the layers and wash the organic extract with additional water (50 ml). Separate the layers again and concentrate the remaining organic extract to provide a residue (19.0 g) of crude duloxetine free amine. % ΔR: 1.0. Monitor the % R enantiomer by chiral HPLC under the following conditions: Column; Diacel Chiralcel® OD-H, 5 micron silica, 4.6×250 mm internal diameter, 40° C.; Solvent: 83% hexane+0.1% DEA−17% isopropanol+0.1% DEA, 1 mL/min; detection UV 230 nm.

EXAMPLE 3

Arylation of (S)-3-Methylamino-1-(2-thienyl)-1-propanol

Charge a 250 ml reactor with Compound Ia (8.56 g, 0.05 mol), potassium hydroxide (12.5 g, 0.06 mol), toluene (100 m)l, 1-fluoronaphthalene (8.77 g, 0.06 mol) and DMSO (10 ml). Heat the resulting suspension to 85° C. over 30 minutes. After 8 h, cool the suspension to ambient temperature and add water (100 ml). Separate the layers and extract the aqueous layer with toluene (50 ml). Wash the combined organic layers with 15% aq. NaCl (50 ml) and concentrate. % ΔR: 2.2. Monitor the % R enantiomer by chiral HPLC under the following conditions: Column; Diacel Chiralcel® OD-H, 5 micron silica, 4.6×250 mm internal diameter, 40° C.; Solvent: 83% hexane+0.1% DEA−17% isopropanol+0.1% DEA, 1 mL/min; detection UV 220 nm.

We claim:

1. A process for preparing (S)-(+)-N-methyl-3-(1-naphthaleneoxy)-3-(2-thienyl)propamine comprising reacting (S)-3-Methylamino-1-(2-thienyl)-1-propanol with potassium hydroxide, and 1-fluoronaphthalene in an organic solvent or mixture of organic solvents wherein said solvent or mixture of organic solvents is a mixture of DMSO and toluene, and the product has a % R less than 20%.

2. A process according to claim 1 wherein the product has a % R less than 10%.

3. A process according to claim 1 wherein the product has a % R less than 6%.

4. A process according to claim 1 further comprising heating the mixture to a temperature of from about 40° C. to 110° C. for about 1 hour to 48 hours.

5. A process for preparing (S)-(+)-N,N-dimethyl-3-(1-naphthalenyloxy)-3-(2-thienyl)propanamine comprising reacting (S)-(−)-N,N-dimethyl-3-(2-thienyl)-3-hydroxypropanamine with potassium hydroxide and 1-fluoronaphthalene in an organic solvent wherein the organic solvent is selected from glyme, diglyme, triglyme, or tetraglyme.

6. A process according to claim 5 wherein the product has a % R less than 20%.

7. A process according to claim 5 wherein the product has a % R less than 10%.

8. A process according to claim 5 wherein the product has a % R less than 6%.

9. A process according to claim 5 further comprising heating the mixture to a temperature of from about 80° C. to 120° C. for about 1 hour to 24 hours.

* * * * *